(12) United States Patent
Lee

(10) Patent No.: US 8,594,797 B2
(45) Date of Patent: Nov. 26, 2013

(54) COMPUTATIONALLY EFFICIENT TECHNIQUE FOR DETERMINING ELECTRODE CURRENT DISTRIBUTION FROM A VIRTUAL MULTIPOLE

(71) Applicant: Boston Scientific Neuromodulation Corporation, Valencia, CA (US)

(72) Inventor: Dongchul Lee, Agua Dulce, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/717,298

(22) Filed: Dec. 17, 2012

(65) Prior Publication Data

US 2013/0158630 A1 Jun. 20, 2013

Related U.S. Application Data

(60) Provisional application No. 61/577,582, filed on Dec. 19, 2011.

(51) Int. Cl.
*A61N 1/34* (2006.01)

(52) U.S. Cl.
USPC .............................................. 607/46; 607/59

(58) Field of Classification Search
USPC .......................................................... 607/46
See application file for complete search history.

(56) References Cited

U.S. PATENT DOCUMENTS

| | | |
|---|---|---|
| 6,516,227 B1 | 2/2003 | Meadows et al. |
| 6,895,280 B2 | 5/2005 | Meadows et al. |
| 6,993,384 B2 | 1/2006 | Bradley et al. |
| 2007/0150036 A1 | 6/2007 | Anderson |
| 2007/0168004 A1 | 7/2007 | Walter |
| 2007/0168007 A1 | 7/2007 | Kuzma et al. |
| 2010/0010566 A1 | 1/2010 | Thacker et al. |
| 2010/0057162 A1 | 3/2010 | Moffitt et al. |
| 2010/0121409 A1 | 5/2010 | Kothandaraman et al. |
| 2011/0106215 A1 | 5/2011 | Moffitt |

OTHER PUBLICATIONS

U.S. Appl. No. 61/452,965, Neurostimulation System for Defining a Generalized Ideal Multipole Configuration, Inventor: Dongchul Lee, filed Mar. 15, 2011.

*Primary Examiner* — Michael Kahelin
(74) *Attorney, Agent, or Firm* — Vista IP Law Group LLP

(57) ABSTRACT

A system and method of providing therapy to a patient using a plurality of electrodes implanted within the patient. A virtual multipole configuration is defined relative to the plurality of electrodes. The distance between each of a group of the electrodes and a virtual pole of the virtual multipole configuration is determined. A stimulation amplitude distribution is determined for the electrode group based on the determined distances, thereby emulating the virtual multipole configuration. Electrical energy is conveyed from the electrode group in accordance with the computed stimulation amplitude distribution.

28 Claims, 9 Drawing Sheets

COMPUTATIONALLY EFFICIENT TECHNIQUE FOR DETERMINING ELECTRODE CURRENT DISTRIBUTION FROM A VIRTUAL MULTIPOLE

RELATED APPLICATION DATA

The present application claims the benefit under 35 U.S.C. §119 to U.S. provisional patent application Ser. No. 61/577,582, filed Dec. 19, 2011. The foregoing application is hereby incorporated by reference into the present application in its entirety.

FIELD OF THE INVENTION

The present inventions relate to tissue stimulation systems, and more particularly, to neurostimulation systems for programming neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) and Peripheral Nerve Field Stimulation (PNFS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different stimulation amplitude distributions (i.e., fractionalized electrode combinations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets, which will typically be those that stimulate all of the target tissue in order to provide the therapeutic benefit, yet minimizes the volume of non-target tissue that is stimulated. The computerized programming system may be operated by a clinician attending the patient in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the painful site. Thus, the navigation session may be used to pinpoint the volume of activation (VOA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neurostimulator (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

Prior to creating the stimulation programs, the Bionic Navigator® may be operated by a clinician in a "manual mode" to manually select the percentage cathodic current and percentage anodic current flowing through the electrodes, or may be operated by the clinician in an "automated mode" to electrically "steer" the current along the implanted leads in real-time (e.g., using a joystick or joystick-like controls), thereby allowing the clinician to determine the most efficacious stimulation parameter sets that can then be stored and eventually combined into stimulation programs. In the context of SCS, current steering is typically either performed in a rostro-caudal direction (i.e., along the axis of the spinal cord) or a medial-lateral direction (i.e., perpendicular to the axis of the spinal cord).

In one novel method, described in U.S. patent application Ser. No. 12/938,282, entitled "System and Method for Mapping Arbitrary Electric Fields to Pre-existing Lead Electrodes," which is incorporated herein by reference, a stimulation target in the form of an ideal (or virtual) target multipole pole (e.g., a virtual bipole or tripole) is defined and the stimulation parameters, including the stimulation amplitude distribution on the electrodes, are computationally determined in a manner that emulates these virtual multipoles. This technique involves defining the virtual multipole, computing field potential values that the virtual multipole creates on an array of spatial observation points, and determining the stimulation amplitude distribution on the electrodes that would result in estimated electrical field potential values at the spatial observation points that best matches the desired field potential values at the spatial observation points. It can be appreciated that current steering can be implemented by moving the virtual multipoles about the leads, such that the appropriate stimulation amplitude distribution for the electrodes is computed for each of the various positions of the virtual multipole. As a result, the current steering can be implemented using an arbitrary number and arrangement of electrodes.

While the computation of the stimulation amplitude distribution on the electrodes to emulate a virtual multipole is quite useful, a computationally intensive optimization technique utilizing an inverse transfer matrix is used to determine the stimulation amplitude distribution, which may not present a significant issue if the computerized programming system has the necessary computational power, but may present a significant issue if the optimization technique is incorporated into a less computationally powerful device, such as a remote control. Furthermore, the computation of the stimulation amplitude distribution on the electrodes may result in electrodes with small percentages of current that do not actively contribute to the electrical stimulation field. A "cleaning algorithm" may be used to null out the electrodes with current percentages below a specified threshold. However, this cleaning algorithm may not provide a smooth transition of the virtual multipole in space during current steering.

There, thus, remains a need for a more computationally efficient technique for determining the stimulation parameters that best emulate a virtual multipole.

SUMMARY OF THE INVENTION

In accordance with a first aspect of the present inventions, a system for an electrical neurostimulator coupled to a plurality of electrodes is provided. The processor is configured for defining a virtual multipole configuration (e.g., a virtual bipole configuration or a virtual tripole configuration) relative to the plurality of electrodes, and determining a distance between each of a group of the electrodes and a virtual pole (e.g., a virtual cathode or a virtual anode) of the virtual multipole configuration.

In one embodiment, the processor is further configured for limiting the number of electrodes in the electrode group to a maximum number. In this case, the processor may further be configured for varying the maximum number of the electrodes in the electrode group in response to a user input. In another embodiment, the processor is further configured for comparing a function of a distance (e.g., a proportional function, a higher order power function, or an exponential function) between each of the plurality of electrodes and the virtual pole to a threshold value, and excluding the electrode from the electrode group based on the comparison.

The processor is further configured for determining a stimulation amplitude distribution for the electrode group based on the determined distances, thereby emulating the virtual multipole configuration. In one embodiment, the processor is configured for determining the stimulation amplitude distribution for the electrode group by computing weights as decreasing functions of the distances (e.g., an inverse proportional function of the respective distance, an inverse higher order power function of the respective distance, or an inverse exponential function of the respective distance), and computing stimulation amplitude values respectively for the electrode group as a function of the computed weights. The stimulation amplitude values may be fractionalized current values, in which case, the processor may be configured for computing a fractionalized current value for each electrode of the electrode group as the quotient of the weight for the each electrode divided by the sum of the weights for the electrode group.

The system further comprises a controller configured for instructing the electrical neurostimulator to convey electrical energy to the electrode group in accordance with the computed stimulation amplitude distribution. The system optionally comprises a user interface configured for generating directional control signals, in which case, the processor may be further configured for modifying the virtual multipole configuration relative to the plurality of electrodes in response to the directional control signals, and repeating the distance determination and stimulation amplitude distribution steps for the modified virtual multipole configuration, and the controller may be further configured for repeating the electrical energy conveyance step for the modified virtual multipole configuration. The system may further comprise telemetry circuitry, in which case, the controller may further be configured for transmitting stimulation parameter sets defining the computed stimulation amplitude distribution to the neurostimulation device via the telemetry circuitry. The system may also comprise a housing containing the processor and controller.

In accordance with a second aspect of the present inventions, a method of providing therapy to a patient using a plurality of electrodes implanted within the patient is provided. The method comprises defining a virtual multipole configuration (e.g., a virtual bipole configuration or a virtual tripole configuration) relative to the plurality of electrodes, and determining a distance between each of a group of electrodes and a virtual pole (e.g., a virtual cathode or a virtual anode) of the virtual multipole configuration.

One method comprises limiting the number of electrodes in the electrode group to a maximum number. In this case, the maximum number of the electrodes in the electrode group may be varied in response to a user input. Another method comprises comparing a function of a distance (e.g., a proportional function, a higher order power function, or an exponential function) between each of the plurality of electrodes and the virtual pole to a threshold value, and excluding the electrode from the electrode group based on the comparison.

The method further comprises determining a stimulation amplitude distribution for the electrode group based on the determined distances, thereby emulating the virtual multipole configuration. The stimulation amplitude distribution for the electrode group may be determined by computing weights as decreasing functions of the distances (e.g., an inverse proportional function of the respective distance, an inverse higher order power function of the respective distance, or an inverse exponential function of the respective distance), and computing stimulation amplitude values respectively for the electrode group as a function of the computed weights. The stimulation amplitude values may be fractionalized current values, in which case, a fractionalized current value can be computed for each electrode of the electrode group as the quotient of the weight for the each electrode divided by the sum of the weights for the electrode group.

The method further comprises conveying electrical energy from the electrode group in accordance with the computed stimulation amplitude distribution. An optional method comprises generating directional control signals, modifying the virtual multipole configuration relative to the plurality of electrodes in response to the directional control signals, and repeating the distance determination, stimulation amplitude distribution, and electrical energy conveyance steps for the modified virtual multipole configuration.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neurostimulator configured to treat urinary incontinence, sleep apnea, shoulder sublaxation, headache, etc.

Figure 1:
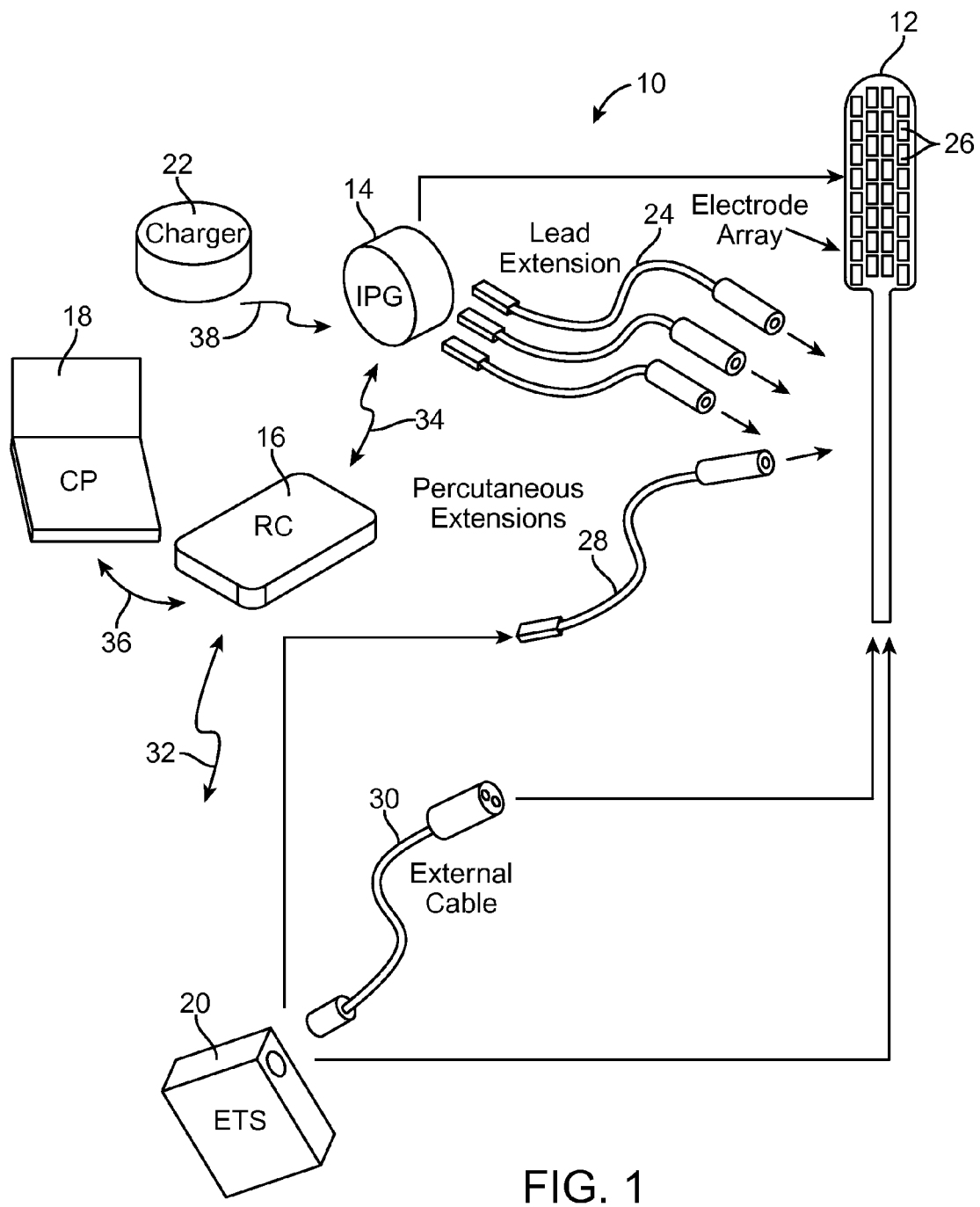
FIG. 1 is a plan view of a Spinal cord Stimulation (SCS) system constructed in accordance with one embodiment of the present inventions.

Turning first to FIG. 1, an exemplary SCS system 10 generally comprises at least one implantable neurostimulation lead 12, an implantable pulse generator (IPG) 14 (or alternatively RF receiver-stimulator), an external remote control RC 16, a Clinician's Programmer (CP) 18, an External Trial Stimulator (ETS) 20, and an external charger 22.

The IPG 14 is physically connected via one or more lead extensions 24 to the neurostimulation lead 12, which carries a plurality of electrodes 26 arranged in an array. The neurostimulation lead 12 is illustrated as a surgical paddle lead in FIG. 1, although as will be described in further detail below, one or more percutaneous stimulation leads can be used in place of the surgical paddle lead 12. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20, which has similar pulse generation circuitry as the IPG 14, also provides electrical stimulation energy to the electrode array 26 in accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation lead 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
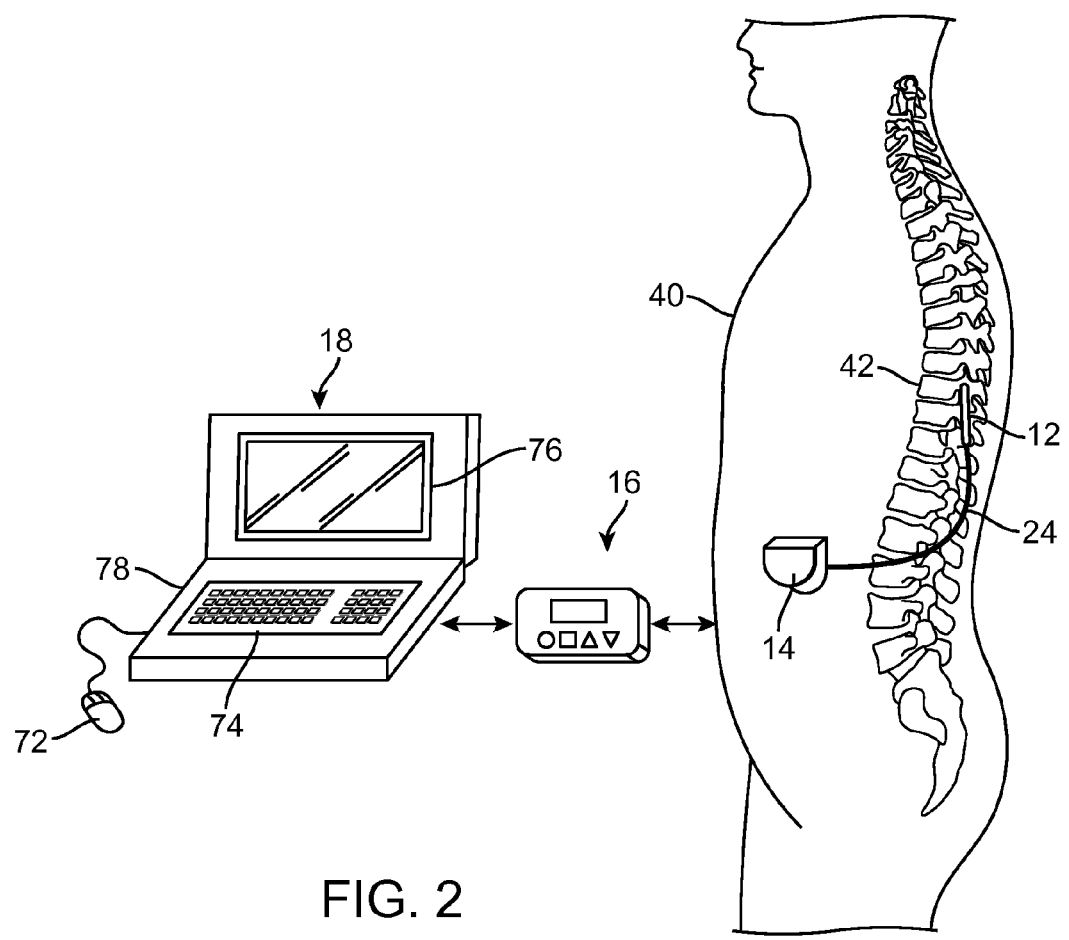
FIG. 2 is a perspective view of the arrangement of the SCS system of FIG. 1 with respect to a patient.

As shown in FIG. 2, the neurostimulation lead 12 is implanted within the spinal column 42 of a patient 40. The preferred placement of the neurostimulation lead 12 is adjacent, i.e., resting upon, the spinal cord area to be stimulated. Due to the lack of space near the location where the neurostimulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 communicates with the IPG 14 via the RC 16.

Figure 3:
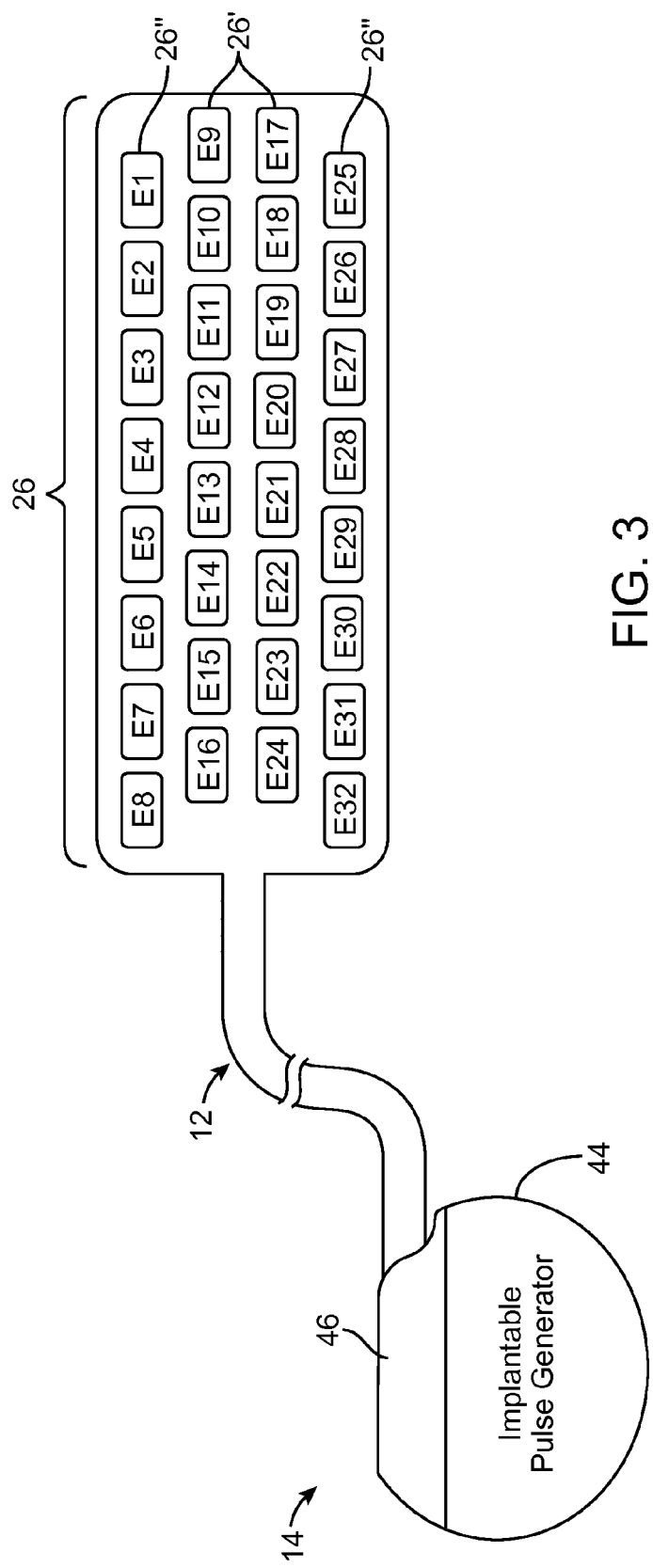
FIG. 3 is a profile view of an implantable pulse generator (IPG) and a surgical paddle lead used in the SCS system of FIG. 1.

Referring to FIG. 3, the IPG 14 comprises an outer case 44 for housing the electronic and other components (described in further detail below), and a connector 46 to which the proximal end of the neurostimulation lead 12 mates in a manner that electrically couples the electrodes 26 to the internal electronics (described in further detail below) within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

In the embodiment illustrated in FIG. 3, the neurostimulation lead 12 takes the form of a surgical paddle lead 12 on which the electrodes 26 (in this case, electrodes E1-E32) are carried. The electrodes 26 are arranged in a two-dimensional array in four columns along the axis of the neurostimulation lead 12. In the illustrated embodiment, the electrodes 26 are arranged in two inner columns of electrodes 26' (electrodes E9-E24), and two outer columns of electrodes 26" (electrodes E1-E8 and E25-E32) that flank and are longitudinally offset from the inner electrode columns. In other embodiments, the outer and inner electrode columns may not be longitudinally offset from each other. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," and U.S. patent application Ser. No. 12/204,094, entitled "Multiple Tunable Central Cathodes on a Paddle for Increased Medial-Lateral and Rostro-Caudal Flexibility via Current Steering, the disclosures of which are expressly incorporated herein by reference.

Figure 4:
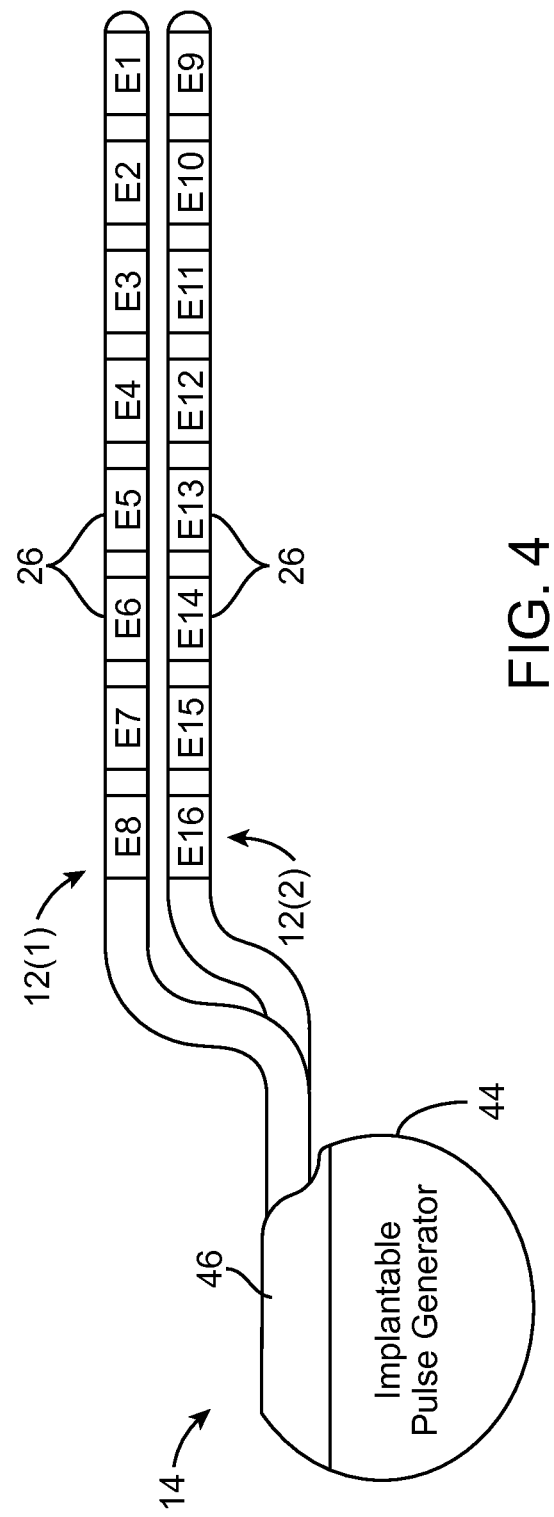
FIG. 4 is a profile view of an implantable pulse generator (IPG) and percutaneous leads used in the SCS system of FIG. 1.

In an alternative embodiment illustrated in FIG. 4, the neurostimulation lead 12 takes the form of a percutaneous stimulation lead on which the electrodes 12 (in this case, electrodes E1-E16) are disposed as ring electrodes. In the illustrated embodiment, two percutaneous leads 12 on which electrodes E1-E8 and E9-E16 are disposed can be used with the SCS system 10. The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

As will be described in further detail below, the IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation phase and an anodic (positive) recharge phase that is generated after the stimulation phase to prevent direct current charge transfer through the tissue, thereby avoiding electrode degradation and cell trauma. That is, charge is delivered through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

In the illustrated embodiment, the IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
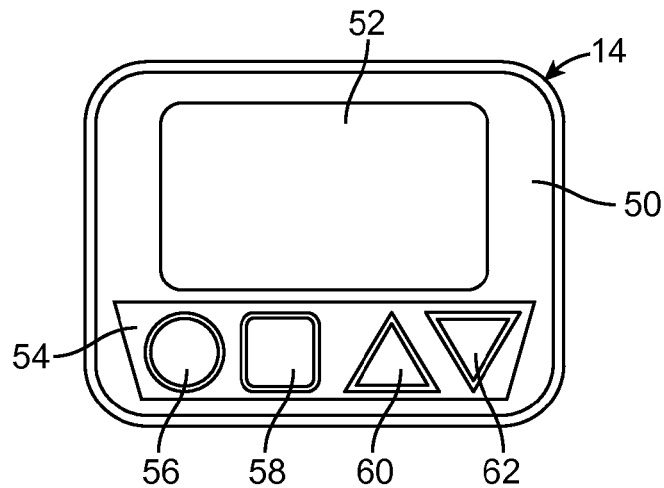
FIG. 5 is front view of a remote control (RC) used in the SCS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touch screen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 6:
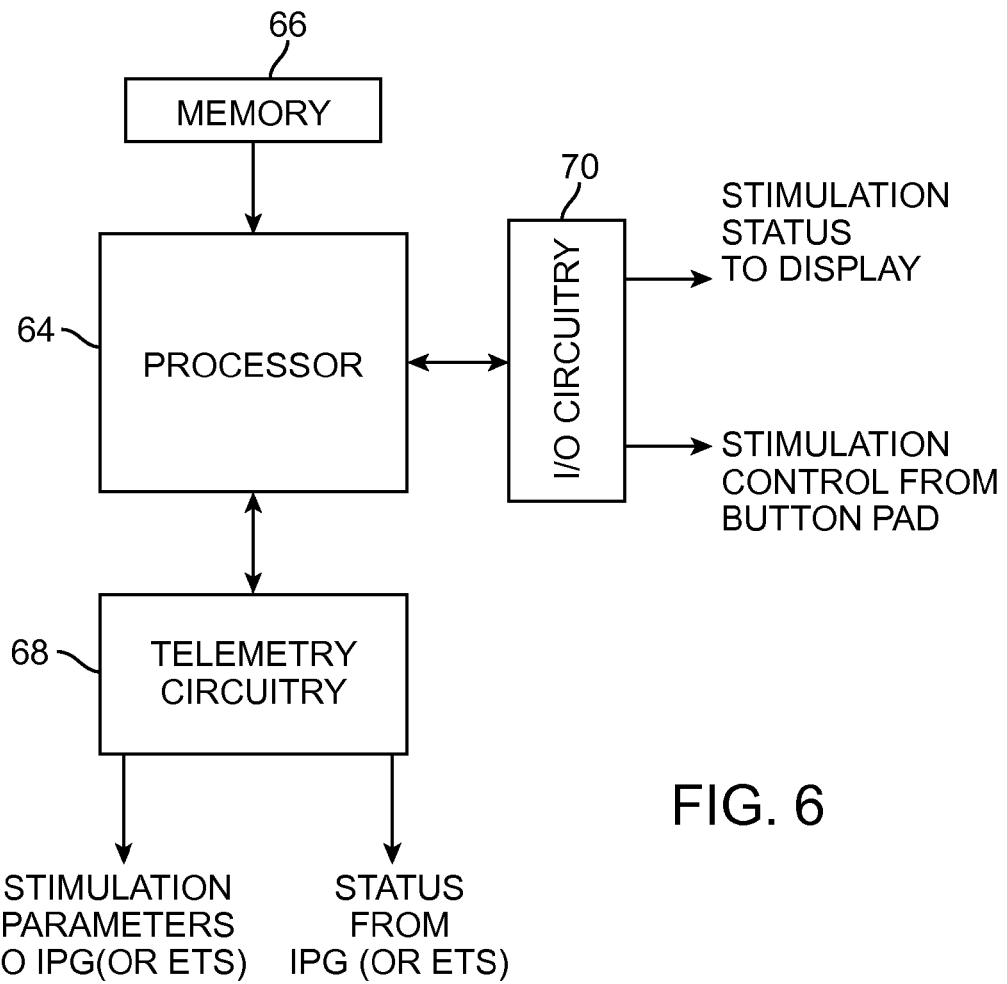
FIG. 6 is a block diagram of the internal components of the RC of FIG. 4.

Referring to FIG. 6, the internal components of an exemplary RC 16 will now be described. The RC 16 generally includes a processor 64 (e.g., a microcontroller), memory 66 that stores an operating program for execution by the processor 64, as well as stimulation parameter sets in a navigation table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 5). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implanted using a PC that has been appropriately configured to include a directional-programming device and programmed to perform the functions described herein. Alternatively, the CP 18 may take the form of a mini-computer, personal digital assistant (PDA), smartphone, etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient response and feedback and for subsequently programming the IPG 14 with the optimum stimulation parameters.

To allow the user to perform these functions, the CP 18 includes a mouse 72, a keyboard 74, and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74. In the illustrated embodiment, the monitor 76 is a conventional screen. Alternatively, instead of being conventional, the monitor 76 may be a digitizer screen, such as touchscreen (not shown), and may be used in conjunction with an active or passive digitizer stylus/finger touch.

Figure 7:
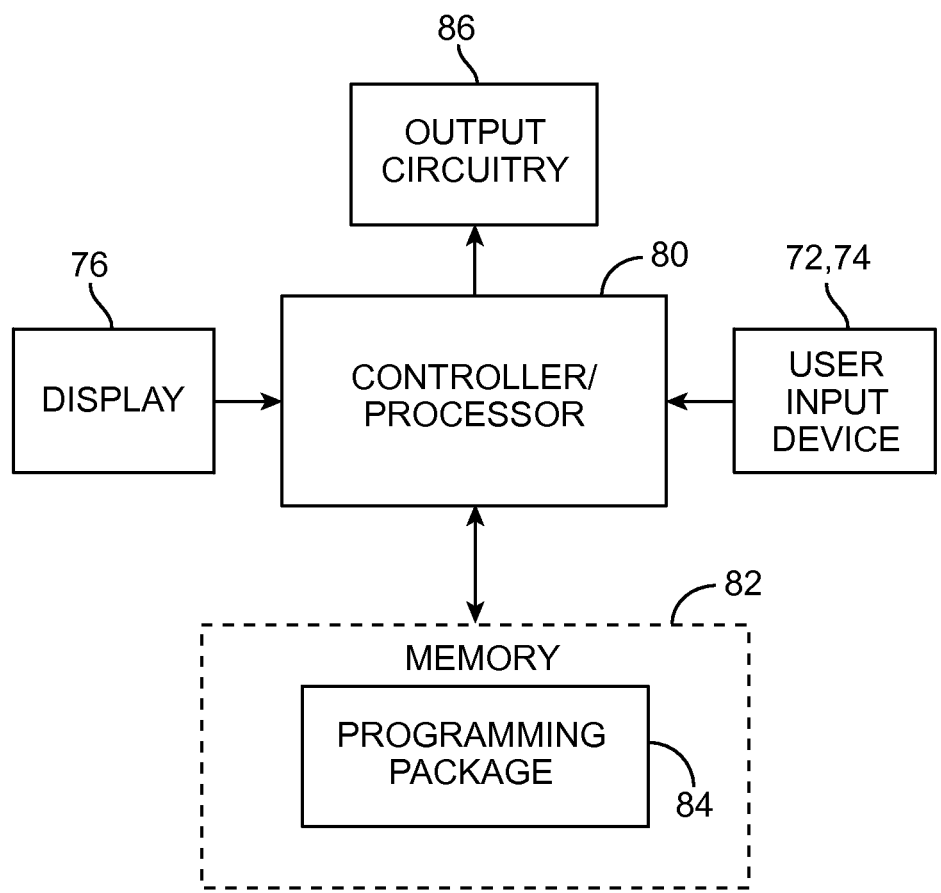
FIG. 7 is a block diagram of the internal components of a clinician's programmer (CP) used in the SCS system of FIG. 1.

As shown in FIG. 7, the CP 18 further includes a controller/processor 80 (e.g., a central processor unit (CPU)) and memory 82 that stores a stimulation programming package 84, which can be executed by the controller/processor 80 to allow the user to program the IPG 14, and RC 16. Notably, while the controller/processor 80 is shown as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by a processor. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16.

Execution of the programming package 84 by the controller/processor 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides a user interface that conveniently allows a user to program the IPG 14 in a manner that emulates an ideal multipole, such as a bipole or tripole, much like in the manner described in U.S. patent application Ser. No. 12/938,282, which was previously incorporated herein by reference. However, in this case, the programming package 84 provides a series of different ideal multipole configurations that can be used to steer electrical current relative to the electrodes 12 in response to directional control signals generated in response to manipulation of a directional programming device, such as one or more of the directional programming devices described above.

Figure 8:
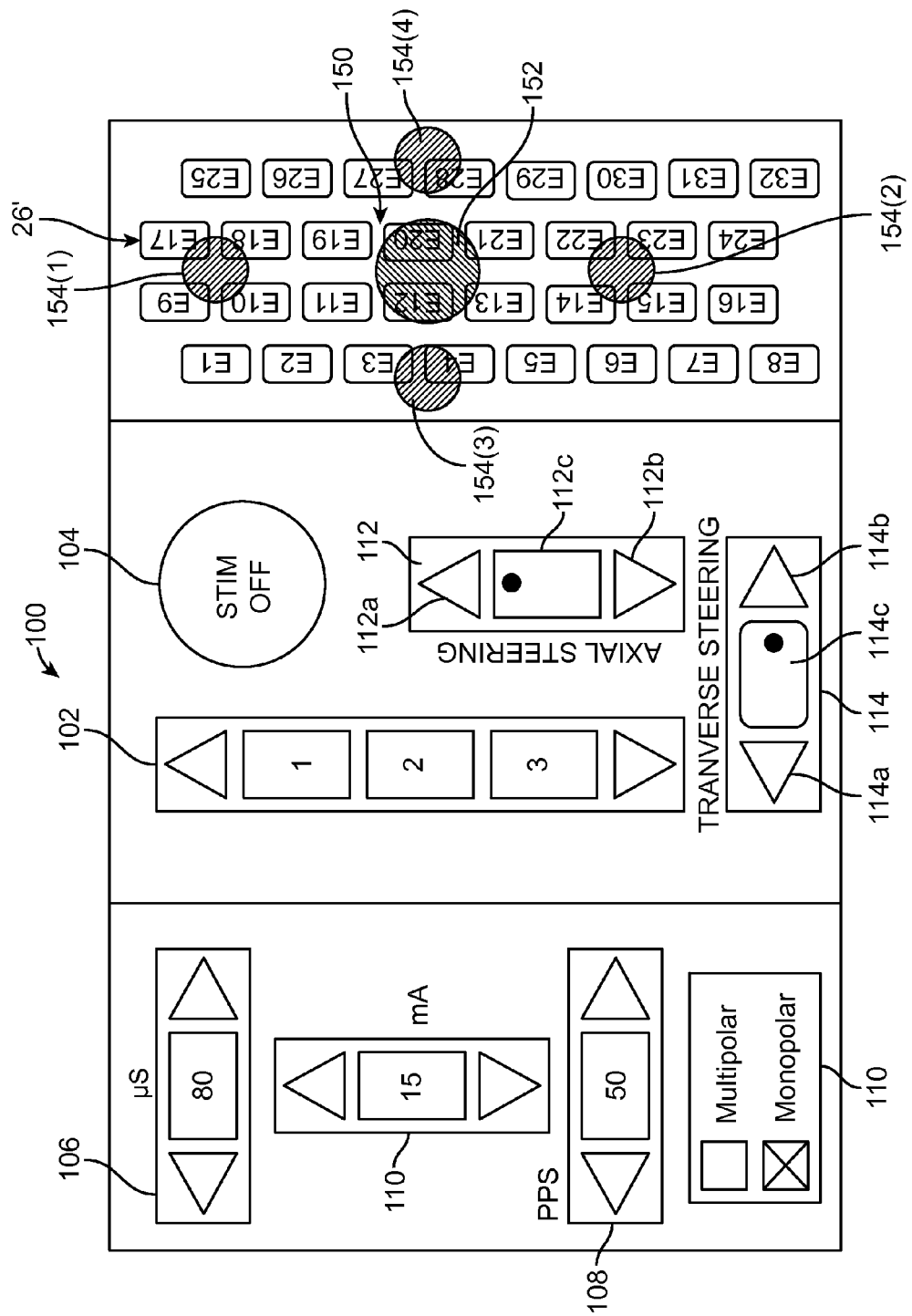
FIG. 8 is a plan view of a programming screen generated by the CP of FIG. 7 for programming the IPG of FIG. 3.

Referring now to FIG. 8, an exemplary programming screen 100 generated by the CP 16 to allow a user to program the IPG 14 will now be described. The programming screen 100 includes various control elements described below that can be actuated to perform various control functions.

A pointing element may be placed on any of the control elements to perform the actuation event. As described above, in the case of a digitizer touch screen, the pointing element will be an actual pointing element (e.g., a finger or active or passive stylus) that can be used to physically tap the screen above the respective graphical control element or otherwise brought into proximity with respect to the graphical control element. In the case of a conventional screen, the pointing element will be a virtual pointing element (e.g., a cursor) that can be used to graphically click on the respective control element.

The programming screen 100 includes an electrode combination control 102 having arrows that can be actuated by the user to select one of four different electrode combinations 1-4. The programming screen 100 further includes a stimulation on/off control 104 that can be alternately actuated initiate or cease the delivery of electrical stimulation energy from the IPG 14 via the selected electrode combination.

The programming screen 100 further includes various stimulation parameter controls that can be operated by the user to manually adjust stimulation parameters for the selected electrode combination. In particular, the programming screen 100 includes a pulse width adjustment control 106 (expressed in microseconds (μs)), a pulse rate adjustment control 108 (expressed in Hertz (Hz)), and a pulse amplitude adjustment control 110 (expressed in milliamperes (mA)). Each control includes a first arrow that can be actuated to decrease the value of the respective stimulation parameter and a second arrow that can be actuated to increase the value of the respective stimulation parameter.

The programming screen 100 also includes a set of axial steering control elements 112 and a set of transverse steering control elements 114. In the illustrated embodiments, the control elements 112, 114, as well as the other control elements discussed herein, are implemented as a graphical icon that can be clicked with a mouse or touched with a finger in the case of a touchscreen. Alternatively, the control elements described herein may be implemented as a joy stick, touchpad, button pad, group of keyboard arrow keys, mouse, roller ball tracking device, horizontal or vertical rocker-type arm switches, etc., that can be pressed or otherwise moved to actuate the control elements.

When any of the axial steering control elements 112 is actuated, control signals are generated in response to which the controller/processor 80 is configured for generating stimulation parameter sets designed to axially displace the locus of the electrical stimulation field (and thus, the volume of activation (VOA)) relative to the axis of the lead 12. Likewise, when any of the transverse steering control elements 114 is actuated, control signals are generated in response to which the controller/processor 80 is configured for generating stimulation parameter sets designed to transversely displace the locus of the electrical stimulation field (and thus, the VOA) relative to the axis of the lead 12.

The control elements 112, 114 may be continually actuated (i.e., by continuously actuating one of the control elements 112, 114, e.g., by clicking on one of the control elements 112, 114 and holding the click (i.e., continuous actuation of the control following the initial "click"), or repeatedly actuating one of the control elements 112, 114, e.g., by repeatedly clicking and releasing one of the control elements 112, 114) to generate a series of control signals in response to which the controller/processor 80 is configured for generating the plurality of stimulation parameter sets. The output telemetry circuitry 86 is configured for transmitting these stimulation parameters sets to the IPG 14.

Preferably, the control signals that are generated in response to the actuation of the control elements 112, 114 or the alternative control elements are directional, meaning that the locus of the electrical stimulation field will be displaced in a defined direction in response to a continual actuation of a single control element irrespective of the current position of the locus electrical stimulation field locus. As will be described in further detail below, the controller/processor 80, in response to the actuation of the control elements 112, 114, first defines a series of ideal multipoles, and computationally determines the stimulation parameters, including the fractionalized current values on each of the electrodes, in a manner that emulates these ideal multipoles.

Each of the sets of control elements 112, 114 takes the form of a double arrow (i.e., two oppositely pointing control element arrows) that can be actuated to modify the electrical stimulation field depending on the mode of operation. For example, an upper arrow control element 112a can be clicked to axially displace (i.e., along the axis of the lead 12) the locus of the electrical stimulation field in the proximal direction; a lower arrow control element 112b can be clicked to axially displace (i.e., along the axis of the lead 12) the locus of the electrical stimulation field in the distal direction; a left arrow control element 114a can be clicked to transversely displace (i.e., perpendicular to the axis of the lead 12) the locus of the electrical stimulation field in the leftward direction; and a right arrow control element 114b can be clicked to transversely displace (i.e., perpendicular to the axis of the lead 12) the locus of the electrical stimulation field in the rightward direction. The control elements 112, 114 also include indicators 112c, 114c for displaying an indication of the locus of the electrical stimulation field relative to the lead 12. In particular, an indicator 112c displays a dot representative of the axial displacement of the electrical stimulation field locus, and an indicator 114c displays a dot representative of the transverse displacement of the electrical stimulation field locus.

The programming screen 100 displays graphical representations of the electrodes 26'. In the illustrated embodiment, each electrode representation 26' takes the form of a closed geometric figure, and in this case a rectangle. In alternative embodiments, the electrode representations 26' can take the form of other types of closed geometric figures, such as circles. The programming screen 100 also displays a graphical rendering of an ideal multipole 150 relative to the electrode array 26.

In one embodiment, the multipole 150 is a generalized multipole that defines five imaginary locations for a central virtual pole 152 and four surrounding virtual poles 154(1)-154(4) (collectively, 154). The generalized multipole 150 is defined with several sets of variable values that are stored in memory 82. These sets of variable values include a set of variable values defining the polarities of the central virtual pole 152 and surrounding virtual poles 154, a set of variable values defining a spatial relationship between the central virtual pole 152 and the electrode array 26, a set of variable values defining a spatial relationship between the surrounding virtual poles 154 and the central virtual pole 152, and a set of variable values defining relative intensities of the surrounding virtual poles 154. In practice, the set of variable values defining the relative intensities of the surrounding virtual poles 154 will typically be defined, such that a tripole or even a bipole configuration results. For example, a virtual tripole configuration arranged in a rostro-caudal manner (vertical tripole) can be defined by setting the intensities for the virtual poles 154(1) and 154(2) to a non-zero value, while setting the intensities for the virtual poles 154(3) and 154(4) to a zero value. A virtual tripole configuration arranged in a mediolateral manner (horizontal tripole) can be defined by setting the intensities for the virtual poles 154(1) and 154(2) to a zero value, while setting the intensities for the virtual poles 154(3) and 154(4) to a non-zero value.

The ideal multipole 150 may be manipulated by the controller/processor 80 relative to the electrode array 26 in response to the control signals generated by actuation of the steering control elements 112, 114. Alternatively, rather than automatically manipulating the ideal multipole 150 in response to the current steering control signals, the ideal multipole 150 may be manually manipulated, e.g., by touching any of the virtual poles with a physical pointing device or otherwise clicked with a virtual pointing device and dragged to a different location relative to the electrode representations 26'. For example, the central virtual pole 152 may be dragged to displace the entire ideal multiple 150 relative to the electrode representations 26' or one of the surrounding virtual poles 154 may be dragged to displace it relative to the central virtual pole 152.

Further details discussing techniques for using a generalized virtual multipole to define various types of multipoles, as well specific techniques for steering current using ideal multipole configurations, are described in U.S. Provisional Patent Application Ser. No. 61/452,965, entitled "Neurostimulation System for Defining A Generalized Ideal Multipole Configuration," which is expressly incorporated herein by reference.

However the virtual multipole configuration is manipulated relative to the electrode array 26, the controller/processor 80 is configured for determining the stimulation amplitude distribution for the electrode array 26 that emulates the virtual multipole configuration in a computationally efficient manner.

Figure 9:
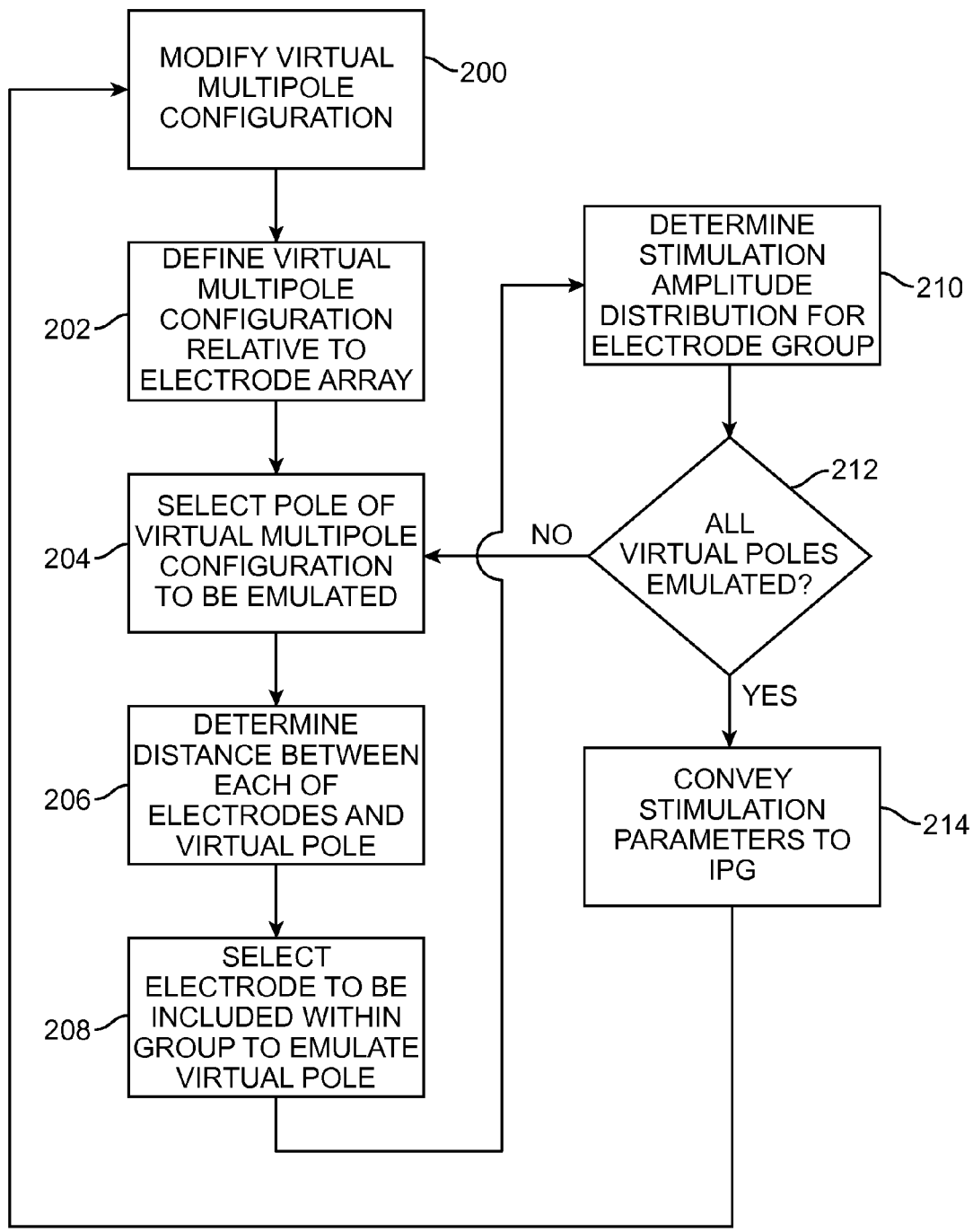
FIG. 9 is a flow diagram illustrating one method of emulating a virtual multipole configuration generated in the programming screen of FIG. 8.

Having described the structure and function of the neurostimulation 10, one method of providing therapy to a patient utilizing the programmer screen 100 shown in FIG. 8 will now be described with reference to FIG. 9. First, the user modifies the virtual multipole configuration 150 (step 200). For example, the user may manipulate the current steering control elements 112, 114 to automatically modify the virtual multipole configuration, or may alternatively, drag the virtual poles to manually modify the virtual multipole configuration. The controller/processor 80 then defines the modified virtual multipole configuration relative to the electrode array 26 (step 202).

Figure 10:
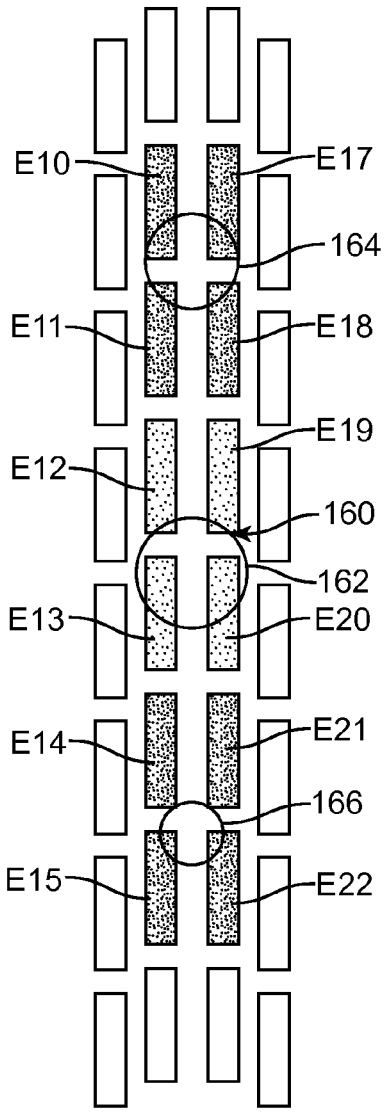
FIG. 10 is a plan view of an exemplary virtual tripole configuration defined relative to an electrode array.

In an example shown in FIG. 10, a vertically oriented virtual tripole configuration 160 is formed from the variable generalized ideal multipole configuration 150. The virtual tripole configuration 160 is shown defined relative to the electrode array 26, and has a central virtual cathode 162, an upper virtual anode 164, and a lower virtual anode 166. The size of each of the poles in the virtual tripole configuration is indicative of the magnitude of current assigned to the respective poles. In the illustrated embodiment, all of the cathodic current is assigned to the central virtual cathode 162, and more of the anodic current is assigned to the upper virtual anode 164 than the lower virtual anode 166 (e.g., 75% of the anodic current can be assigned to the upper virtual anode 164 and 25% of the anodic current can be assigned to the lower virtual anode 166).

Next, the controller/processor 80 selects a pole of the virtual multipole configuration 150 to be emulated (step 204), determines a distance between each of the electrodes 26 and the selected virtual pole (step 206), and based on these determined distances, selects certain ones of these electrodes 26 to be included within a group of the electrodes 26 that will emulate the selected virtual pole (step 208). Because the controller/processor 80 has already defined the virtual multipole configuration 150 relative to the electrode array 26, the controller/processor 80 need only perform simple coordinate system computations in determining the distances between the electrodes 26 and each of the virtual poles.

In an optional embodiment, a clustering algorithm can be used to determine electrodes that are in close proximity to each other. This may be useful in the case where electrode clusters are separated from each other by a relatively long distance, such that electrodes from different clusters would not be selected to emulate a particular virtual pole. Rather, only electrodes from the one cluster that is closest in proximity to the virtual pole should be selected to be included within the electrode group that emulates the virtual pole. In this case, the electrodes that will be ultimately used to emulate the virtual pole will only be selected from this electrode cluster.

In the illustrated embodiment, the number of electrodes in the group is limited to a maximum number (e.g., four), although the number of electrodes in the group may be selected to be less than the maximum number (e.g., if a virtual pole is located directly in the center of an electrode, only one electrode is needed to emulate that electrode, or if less than the maximum number of electrodes are adjacent the virtual pole). This maximum number can be fixed or can be varied by the user (e.g., via a control element (not shown) in the programming screen 100) in order to control the focus/blur of the resulting stimulation. In another embodiment, there is no maximum number of electrodes in the group, but rather, the number of electrodes in the group may be variable. For example, if the density of the electrodes adjacent the virtual pole is relatively high, more electrodes can be selected for the group. On the contrary, if the density of the electrodes adjacent the virtual pole is relatively low, less electrodes can be selected for the group.

Preferably, the electrodes that are closest to the virtual pole to be emulated are selected to be included within the electrode group. For example, as illustrated in FIG. 10, the four electrodes E10, E11, E18, and E19 are closest in proximity to the upper virtual anode 164, and are thus, selected to be included within an electrode group for the upper virtual anode 164; the four electrodes E12, E13, E20, and E21 are closest in proximity to the central virtual cathode 162, and are thus, selected to be included within an electrode group for the central virtual cathode 162; and the four electrodes E14, E15, E22, and E23 are closest in proximity to the lower virtual anode 166, and are thus, selected to be included within an electrode group for the lower virtual anode 166.

When determining the electrodes to be included within a group, the controller/processor 80 may optionally compare a function of a distance between each of the electrodes 26 and the relevant virtual pole to a threshold value, and then exclude certain ones of the electrodes 26 from the group based on the comparison. In essence, the electrodes that are too far away from the virtual pole to generate an electrical field having any significant emulation effect on the virtual pole will be eliminated from the electrode group.

As one example, the function of the distance may be a proportional function (i.e., $A_1*(\text{distance})$, where $A_1$ is a constant). As another example, the function of the distance may be a higher order power function (i.e., $A_1*(\text{distance})^{A_2 x}$, where $A_1$ and $A_2$ are each constants, and x is an integer equal to 2 or more) or an exponential function (i.e., $A_1 e^{A_2 * distance}$, where $A_1$ and $A_2$ are each constants). In this manner, the exponential decay of the electrical field can be taken into account when determining which electrodes are too far away to have a significant effect on emulating the virtual pole.

Because an electrical field is directional, the direction of each electrode relative to the virtual pole may be relevant (e.g., the horizontal distance may be more relevant to the vertical distance, or vice versa). In this case, the function of the distance may take into account the x-component (horizontal direction) and y-component (vertical direction). For example, the function of the distance may be $A_1 e^{A_2 * distance\_x} * e^{A_3 * distance\_y}$, where $A_1, A_2$, and $A_3$ are each constants, distance_x is the x-component of the distance between the electrode and the virtual pole, and distance_y is the y-component of the distance between the electrode and the virtual pole. As another example, the function of the distance may be $A_1 e^{A_2 * distance\_x} + A_3 e^{A_4 * distance\_y}$, where $A_1, A_2, A_3$, and $A_4$ are each constants, distance_x is the x-component of the distance between the electrode and the virtual pole, and distance_y is the y-component of the distance between the electrode and the virtual pole.

In the examples illustrated above, the function of the distance between each electrode and the relevant virtual pole can be compared to a threshold value, and if the function of the distance is greater than the threshold value, the electrode will be excluded from the group. Alternatively, the function of the distance between each electrode and the relevant virtual pole can be an inverse of the functions discussed above, in which case, the electrode will be excluded from the group if the function of the distance is less than the threshold value.

Next, the controller/processor 80 determines a stimulation amplitude distribution for the electrode group based on the distances between the electrodes of the group and the virtual pole, thereby emulating the virtual pole (step 210). Such distances were previously determined in step 206 in order to determine the electrodes to be included in the group. In the illustrated embodiment, the stimulation amplitude distribution is defined as fractionalized electrical current values that are assigned to the respective electrodes, such that the values for each pole totals to 100. However, in alternative embodiments, the stimulation amplitude values may be normalized current or voltage values (e.g., 1-10), absolute current or voltage values (e.g., mA or V), etc. Furthermore, the stimulation amplitude values may be parameters that are a function of current or voltage, such as charge (current amplitude× pulse width) or charge injected per second (current amplitude×pulse width×rate (or period)).

Based on the premise that the further the electrode is from the virtual pole, the less the electrode contributes to emulating the virtual pole, the controller/processor 80 preferably determines the stimulation amplitude distribution by computing weights as decreasing functions of the distances, and computing the stimulation amplitude values respectively for the electrode group as a function of the computed weights.

As one example, the decreasing function of the distance may be an inverse proportional function (i.e., $$\frac{A_1}{\text{distance}},$$

where $A_1$ is a constant). As another example, the decreasing function of the distance may be an inverse higher order power function of the distance (i.e., $A_1*(\text{distance})^{-A_2x}$, where $A_1$ and $A_2$ are each constants, and x is an integer equal to 2 or more) or an inverse exponential function of the distance (i.e., $A_1 e^{-A_2*\text{distance}}$, where $A_1$ and $A_2$ are each constants). In this manner, the exponential decay of the electrical field can be taken into account when determining the stimulation amplitude value of the electrode.

As previously discussed, because an electrical field is directional, the direction of each electrode relative to the virtual pole may be relevant. In this case, the decreasing function of the distance may take into account the x-component (horizontal direction) and y-component (vertical direction). For example, the decreasing function of the distance may be $A_1 e^{-A_2*\text{distance}\_x} * e^{-A_3*\text{distance}\_y}$, where $A_1$, $A_2$, and $A_3$ are each constants, distance_x is the x-component of the distance between the electrode and the virtual pole, and distance_y is the y-component of the distance between the electrode and the virtual pole. As another example, the decreasing function of the distance may be $A_1 e^{-A_2*\text{distance}\_x} + A_3 e^{-A_4*\text{distance}\_y}$, where $A_1$, $A_2$, $A_3$, and $A_4$ are each constants, distance_x is the x-component of the distance between the electrode and the virtual pole, and distance_y is the y-component of the distance between the electrode and the virtual pole.

Figure 11A:
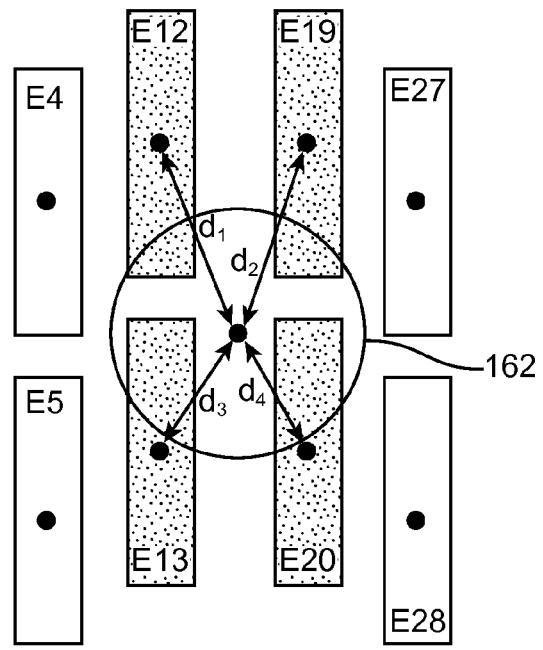
FIGS. 11a and 11b are plan views of the virtual cathode of the virtual tripole configuration defined relative to a group of electrodes used to emulate the virtual cathode.
Figure 11B:
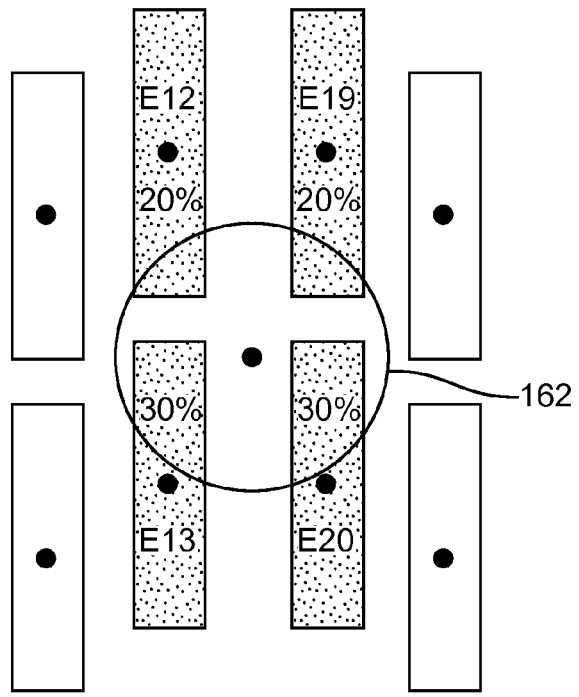

As one example, with reference to FIG. 11a and 11b, electrodes E12, E13, E19, and E20 are closest to the central virtual cathode 162 of the virtual tripole configuration 160, and are selected to be included in the group of electrodes that will emulate the central virtual cathode 162. The distances $d_1$ and $d_2$ respectively between electrodes E12 and E19 and the central virtual cathode 162 are equal to each other, and the distances $d_3$ and $d_4$ respectively between electrodes E13 and E20 and the central virtual cathode 162 are equal to each other, but less than the distances $d_1$ and $d_2$. As such, the stimulation amplitude values for electrodes E13 and E20 are equal to each other, and the stimulation amplitude values for electrodes E12 and E19 are equal to each other, but less than the stimulation amplitude values for electrodes E13 and E20.

In the case where the stimulation amplitude values are fractionalized current values, the stimulation amplitude value for each electrode in the electrode group may be computed as the quotient of the weight for the electrode divided by the sum of the weights for the electrode group. For example, if the weights for electrodes E12, E13, E19, and E20 are as follows: $w_{12}=2$, $w_{13}=3$, $w_{19}=2$, $w_{20}=3$, then the fractionalized electrical current for the electrode group can be computed using the equation:

$$E_{12}(\%) = \frac{w_{12}}{w_{12}+w_{13}+w_{19}+w_{20}} = \frac{2}{2+3+2+3} = \frac{2}{10} = 20\%;$$

$$E_{13}(\%) = \frac{w_{13}}{w_{12}+w_{13}+w_{19}+w_{20}} = \frac{3}{2+3+2+3} = \frac{3}{10} = 30\%;$$

$$E_{19}(\%) = \frac{w_{19}}{w_{12}+w_{13}+w_{19}+w_{20}} = \frac{2}{2+3+2+3} = \frac{2}{10} = 20\%; \text{ and}$$

$$E_{20}(\%) = \frac{w_{20}}{w_{12}+w_{13}+w_{19}+w_{20}} = \frac{3}{2+3+2+3} = \frac{3}{10} = 30\%.$$

Notably, if there is only a single virtual pole of a particular polarization (e.g., the central virtual cathode 162), the total fractionalized current for each electrode group will equal 100%. However, if there are multiple virtual poles of the same polarization (e.g., the upper virtual cathode 164 and the lower virtual cathode 166), the fractionalized electrical current will all electrode groups associated with the same polarized virtual poles will total 100%; that is, the fractionalized electrical current for each electrode group will total less than 100%. In the preferred embodiment, the total fractionalized electrical current for each electrode group is proportional to the fractionalized electrical current for the virtual pole associated with the electrode group. For example, if 75% of the anodic current is assigned to the upper virtual anode 164, and 25% of the anodic current is assigned to the lower virtual anode 166, the fractionalized electrical current for the electrode group (e.g., electrodes E10, E11, E18, and E19) selected for the upper virtual anode 164 will total 75%, and the fractionalized electrical current for the electrode group (e.g., electrodes E14, E15, E22, and E23) selected for the lower virtual anode 166 will be 25%.

Once the stimulation amplitude distribution for the electrode group that emulates the currently selected virtual pole is computed, the controller/processor 80 determines whether all of the poles of the virtual multipole configuration has been emulated (step 212). If all the poles of the virtual multipole configuration have not been emulated, the controller/processor 80 emulates another pole of the virtual multipole configuration 150 (steps 204-210). If all the poles of the virtual multipole configuration have been emulated, the controller/processor 80 conveys stimulation parameters defining the stimulation amplitude distribution to the IPG 14 via the telemetry circuitry 86 (step 214). The IPG 14 will then convey electrical stimulation energy to the active electrodes 26 in accordance with the stimulation parameters. If the virtual multipole configuration is modified at step 200, the modified virtual multipole configuration may be emulated by repeating steps 202-214.

Although the foregoing techniques have been described as being implemented in the CP 18, it should be noted that this technique may be alternatively or additionally implemented in the RC 16, and the processing functions of the technique can even be performed in the IPG 14. Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system for an electrical neurostimulator coupled to a plurality of electrodes, comprising:

a processor configured for defining a virtual multipole configuration relative to the plurality of electrodes, determining a distance between each of a group of the electrodes and a virtual pole of the virtual multipole configuration, and determining a stimulation amplitude distribution for the electrode group based on the determined distances, thereby emulating the virtual multipole configuration; and a controller configured for instructing the electrical neurostimulator to convey electrical energy to the electrode group in accordance with the computed stimulation amplitude distribution.

2. The system of claim 1, wherein the virtual pole is one of a virtual cathode and a virtual anode.

3. The system of claim 1, wherein the virtual multipole configuration is one of a virtual bipole configuration and a virtual tripole configuration.

4. The system of claim 1, wherein the processor is further configured for limiting the number of electrodes in the electrode group to a maximum number.

5. The system of claim 4, wherein the processor is further configured for varying the maximum number of the electrodes in the electrode group in response to a user input.

6. The system of claim 1, wherein the processor is further configured for comparing a function of a distance between each of the plurality of electrodes and the virtual pole to a threshold value, and excluding the each electrode from the electrode group based on the comparison.

7. The system of claim 6, wherein the function of the distance is a proportional function.

8. The system of claim 6, wherein the function of the distance is one of a higher order power function and an exponential function.

9. The system of claim 1, wherein the processor is configured for determining the stimulation amplitude distribution for the electrode group by computing weights as decreasing functions of the distances, and computing stimulation amplitude values respectively for the electrode group as a function of the computed weights.

10. The system of claim 9, wherein each of the weights is computed as an inverse proportional function of the respective distance.

11. The system of claim 9, wherein each of the weights is computed as one of an inverse higher order power function of the respective distance and an inverse exponential function of the respective distance.

12. The system of claim 9, wherein the stimulation amplitude values are fractionalized current values, and the processor is configured for computing a fractionalized current value for each electrode of the electrode group as the quotient of the weight for the each electrode divided by the sum of the weights for the electrode group.

13. The system of claim 1, further comprising a user interface configured for generating directional control signals, wherein the processor is further configured for modifying the virtual multipole configuration relative to the plurality of electrodes in response to the directional control signals, and repeating the distance determination and stimulation amplitude distribution steps for the modified virtual multipole configuration, and the controller is further configured for repeating the electrical energy conveyance step for the modified virtual multipole configuration.

14. The system of claim 1, further comprising telemetry circuitry, wherein the controller is further configured for transmitting stimulation parameter sets defining the computed stimulation amplitude distribution to the neurostimulation device via the telemetry circuitry.

15. The system of claim 1, further comprising a housing containing the processor and controller.

16. A method of providing therapy to a patient using a plurality of electrodes implanted within the patient, comprising:

defining a virtual multipole configuration relative to the plurality of electrodes;

determining a distance between each of a group of the electrodes and a virtual pole of the virtual multipole configuration;

determining a stimulation amplitude distribution for the electrode group based on the determined distances, thereby emulating the virtual multipole configuration; and conveying electrical energy from the electrode group in accordance with the computed stimulation amplitude distribution.

17. The method of claim 16, wherein the virtual pole is one of a virtual cathode and a virtual anode.

18. The method of claim 16, wherein the virtual multipole configuration is one of a virtual bipole configuration and a virtual tripole configuration.

19. The method of claim 16, further comprising limiting the number of electrodes in the electrode group to a maximum number.

20. The method of claim 19, further comprising varying the maximum number of the electrodes in the electrode group in response to a user input.

21. The method of claim 16, further comprising comparing a function of a distance between each of the plurality of electrodes and the virtual pole to a threshold value, and excluding the each electrode from the electrode group based on the comparison.

22. The method of claim 21, wherein the function of the distance is a proportional function.

23. The method of claim 21, wherein the function of the distance is one of a higher order power function and an exponential function.

24. The method of claim 16, wherein determining the stimulation amplitude distribution for the electrode group comprises computing weights as decreasing functions of the distances, and computing stimulation amplitude values respectively for the electrode group as a function of the computed weights.

25. The method of claim 24, wherein each of the weights is computed as an inverse proportional function of the respective distance.

26. The method of claim 24, wherein each of the weights is computed as one of an inverse higher order power function of the respective distance and an inverse exponential function of the respective distance.

27. The method of claim 24, wherein the stimulation amplitude values are fractionalized current values, and the fractionalized current value for each electrode of the electrode group is computed as the quotient of the weight for the each electrode divided by the sum of the weights for the electrode group.

28. The method of claim 16, further comprising:
generating directional control signals;
modifying the virtual multipole configuration relative to the plurality of electrodes in response to the directional control signals; and
repeating the distance determination, stimulation amplitude distribution, and electrical energy conveyance steps for the modified virtual multipole configuration.

* * * * *